(12) United States Patent
Tsunehiro

(10) Patent No.: US 9,380,933 B2
(45) Date of Patent: Jul. 5, 2016

(54) METHOD AND SYSTEM FOR DETERMINING POWER OF INTRAOCULAR LENS TO BE INSERTED

(71) Applicant: SCHOOL JURIDICAL PERSON KITASATO INSTITUTE, Tokyo (JP)

(72) Inventor: Shuntaro Tsunehiro, Sagamihara (JP)

(73) Assignee: SCHOOL JURIDICAL PERSON KITASATO INSTITUTE, Tokyo (JP)

( * ) Notice: Subject to any disclaimer, the term of this patent is extended or adjusted under 35 U.S.C. 154(b) by 0 days.

(21) Appl. No.: 14/564,754

(22) Filed: Dec. 9, 2014

(65) Prior Publication Data

US 2015/0092162 A1 Apr. 2, 2015

Related U.S. Application Data

(63) Continuation of application No. PCT/JP2013/065951, filed on Jun. 10, 2013.

(30) Foreign Application Priority Data

Jun. 14, 2012 (JP) ................................. 2012-135160

(51) Int. Cl.
*A61B 3/00* (2006.01)
*A61B 3/10* (2006.01)
*A61F 2/16* (2006.01)

(52) U.S. Cl.
CPC .............. *A61B 3/0025* (2013.01); *A61B 3/0041* (2013.01); *A61B 3/102* (2013.01); *A61F 2/16* (2013.01)

(58) Field of Classification Search
CPC ............ A61F 2/16; A61F 2009/00872; A61F 9/0017; A61F 2/14

USPC ............... 351/246, 205; 623/6.13, 6.37, 6.51, 623/6.54
See application file for complete search history.

(56) References Cited

U.S. PATENT DOCUMENTS 5,282,852 A * 2/1994 Capetan .................... A61F 2/16
623/6.11
5,968,095 A 10/1999 Norrby
(Continued)

FOREIGN PATENT DOCUMENTS

JP 07-000431 A 1/1995
JP H11-506361 A 6/1999
(Continued)

OTHER PUBLICATIONS

English Translated International Search Report issued for International Application No. PCT/JP2013/065951 dated Jul. 2, 2013, 3 pages.
(Continued)

*Primary Examiner* — Hung Dang
(74) *Attorney, Agent, or Firm* — Rothwell, Figg, Ernst & Manbeck, P.C.

(57) ABSTRACT

The present invention accurately predicts postoperative intraocular lens position on the basis of a shape image of the crystalline lens obtained by an optical interference tomographic imaging device. This makes it possible to reduce the postoperative refractive error and determine the power of the intraocular lens. The present invention comprises: a step for finding by computer the equatorial position, which is the site of maximum diameter in the crystalline lens, from the morphology of the crystalline lens obtained from a tomographic image of the patients eye generated by the optical interference tomographic imaging device; and a step for estimating the position of the intraocular lens from the equatorial position thus found.

10 Claims, 13 Drawing Sheets

(56) References Cited

U.S. PATENT DOCUMENTS

| | | |
|---|---|---|
| 2008/0297724 A1 | 12/2008 | Shimizu et al. |
| 2010/0125331 A1 | 5/2010 | Simpson |
| 2010/0134760 A1 | 6/2010 | Salvati et al. |
| 2013/0107208 A1 | 5/2013 | Endo et al. |
| 2015/0216410 A1* | 8/2015 | Shammas ............ A61B 3/1005 351/246 |

FOREIGN PATENT DOCUMENTS

| | | |
|---|---|---|
| JP | 3779998 B2 | 3/2006 |
| JP | 2007-021147 A | 2/2007 |
| JP | 2008-122295 A | 5/2008 |
| JP | 2008-295973 A | 12/2008 |
| JP | 2009-000354 A | 1/2009 |
| JP | 2010-119583 A | 6/2010 |
| JP | 2010-119853 A | 6/2010 |
| JP | 2012-054010 A | 2/2012 |
| JP | 2013-094410 A | 5/2013 |
| WO | 2008029506 A1 | 3/2008 |
| WO | 2011026068 A2 | 3/2011 |

OTHER PUBLICATIONS

H. Furukawa, et al., "Full-range imaging of eye accommodation by high-speed long-depth range optical frequency domain imaging," Biomedical Optics Express; 2010; vol. 1; No. 5: pp. 1491-1501 (11 pages).

S. Norrby, "Sources of error in intraocular lens power calculation;" J Cataract Refract Surg.; 2008; Vo. 34; pp. 368-376 (9 pages).

J.A. Retzlaff, et al., "Development of SRK/T intraocular lens implant power calculation formula;" J Cataract Refract Surg.; 1990; vol. 16; pp. 333-340 (8 pages).

Office Action issued for Japanese Patent Application No. 2014-521318 dated Oct. 6, 2015 with English translation (4 pages).

\* cited by examiner

METHOD AND SYSTEM FOR DETERMINING POWER OF INTRAOCULAR LENS TO BE INSERTED

CROSS-REFERENCE TO RELATED APPLICATIONS

This application is a continuation of International Application No. PCT/JP2013/065951, filed on Jun. 10, 2013, herein incorporated by reference. Further, this application is based upon and claims the benefit of priority from the prior Japanese Patent Application No. 2012435160, filed on Jun. 14, 2012 entire contents of which are incorporated herein by reference.

BACK GROUND OF THE INVENTION

1. Field of the Invention

The present invention relates to a method and a system that determine the power of postoperative intraocular lens to be inserted using a tomographic image of an anterior ocular segment generated by a tomographic imaging apparatus.

2. Background of the Related Art

Cataract is a disease in which the protein in the crystalline lens is denatured to opacify the crystalline lens, leading to poor eyesight, blurry vision, and the like. A cataract operation is performed to remove the cataract, and in approximately all of such cases, the opacified crystalline lens is removed, and an artificial intraocular lens is inserted instead of the removed crystalline lens.

In the cataract operation, a round hole of diameter 5 to 6 mm is formed in an anterior surface (anterior capsule) of a bladder of the crystalline lens (hereinafter referred to as the crystalline lens capsule), and only the internal opacified portion is emulsified and sucked using an instrument that emits ultrasonic waves. That is, the crystalline lens capsule is substantially wholly left, and after the emulsification and suction of the opacified portion, the artificial intraocular lens is inserted into the empty capsule.

The intraocular lens has a design determined depending on the type of the intraocular lens. The intraocular lens has an optical section formed of crosslinking acryl polymer, silicon, or the like to serve as a lens and a support section formed using PVDF (polyvinylidene fluoride) or the like to make adjustment such that the optical section is located in the center.

For the operation, what refractive index results from operation when an intraocular lens with what power is inserted is predicted based on the cornea refractive power of the eye to be operated on, an ocular axial length, and the like. Then, the intraocular lens to be inserted is determined.

A large portion of the prediction is taken up by prediction of a position where the intraocular lens is fixed after the operation. This is because determining the fixing position of the intraocular lens allows the position of a focus formed by the intraocular lens to be calculated from other parameters such as the refractive index of a passing medium, a passing distance, and the cornea refractive index. In fact, Sverker Norrby, an author of Non-Patent Literature 2, states that 35% of the causes of errors in postoperative refractive index are based on the prediction of the postoperative intraocular lens.

In the conventional prediction method, the fixing position of the intraocular lens is predicted based only on the cornea refractive power and the ocular axial length as described in Patent Literature 1. However, a sufficient prediction accuracy fails to be obtained, and in clinical experiences, the resultant predicted postoperative refraction value and the actual postoperative refraction value frequently fail to match. For actual patients, if the postoperative refraction value deviates to a near-sighted side or a far-sighted side even though an intraocular lens predicted to make the patient emmetropic has been inserted, a sufficient uncorrected vision fails to be achieved, preventing satisfaction from being obtained.

Thus, for a reduction in postoperative refraction errors, it is important to accurately determine the fixing position of the intraocular lens. Various schemes for predicting postoperative refraction have been proposed and employed.

The results of a survey for the members of Japanese Society of Cataract and Refractive Surgery conducted in 2010 indicate that 3% of the questionees use SRK-1, 27% of the questionees use SRK-II, 61% of the questionees use SRK-T, and 9% of the questionees use other schemes.

In the SRK/T scheme (see Non-Patent Literature 1) used by 61% of the questionees, the position of the intraocular lens is estimated based on the radius of curvature of the cornea, the ocular axial length, and the A constant of the crystalline lens.

FIG. 1 is a diagram schematically representing the insertion position of the intraocular lens for description of the SRK/T scheme.

A corrected ocular axial length LC is obtained by, for an ocular axial length $L \leq 24.2$, setting LC=L1, or for $L1>24.2$, correcting the ocular axial length L1 using a quadratic equation. Subsequently, also using a cornea refractive power K (=337.5/a cornea radius of curvature r) determined from the cornea radius of curvature r, a cornea diameter w is calculated in accordance with the following Formula (1).

$$w = -5.41 + 0.58412 \times LC + 0.098 \times K \qquad (1)$$

Then, the height H of a cornea dome is determined in accordance with the Pythagorean theme as illustrated in the following Formula (2).

Height of cornea dome H $$H = r - \sqrt{r^2 - \left(\frac{w}{2}\right)^2} \qquad (2)$$

Then, the position C1 of the intraocular lens is determined by adding a constant (offset Ofst: the distance from a calculated iris surface to the center (principal point) of the intraocular lens (TOL)) determined from an eigenvalue A constant unique to the type of the intraocular lens, to the height of the cornea dome, as illustrated in the following Formula (3).

$$C1(\text{=postoperative predicted anterior chamber depth}) = H + Ofst \qquad (3)$$

However, this scheme poses various problems. For example, an increased ocular axial length L1 reduces $r^2$ in Formula (2), which represents the height of the cornea dome, below $(w/2)^2$ to make the content of the square negative. This frequently leads to a failure to achieve the correct calculations. Furthermore, the actual offset Ofst is not a constant defined only by the intraocular lens.

CITATION LIST

Patent Literature

Patent Literature 1: Japanese Patent No. 3779998
Patent Literature 2: Japanese Publication No. 2012-504010 of PCT Application Non-Patent Literature Non-Patent Literature 1: Development of the SRK/T intraocular lens implant power calculation formula: John A. Retzlaff, Donald R. Sanders, Manus C. Kraff, J cataract refract surg. 1990

Non-Patent Literature 2: Sources of error in intraocular lens power calculation. 3 Cataract Refract Surg. 2008: Sverter Norrby Non-Patent Literature 3: Full-range imaging of eye accommodation by high-speed long-depth range optical frequency domain imaging: Hiroyuki Furukawa, Hideaki Hiro-Oka, Nobuyuki Satoh, Reiko Yoshimura, Donghak Choi, Motoi Nakanishi, Akihiko Igarashi, Hitoshi Ishikawa, Kohji Ohbayashi, and Kimiya Shimizu, 1 Dec. 2010/Vol. 1, No. 5/BIOMEDICAL OPTICS EXPRESSIONS 1491

SUMMARY OF THE INVENTION

Thus, with the foregoing in view, it is an object of the present invention to provide a method and a system that accurately determine the power of an intraocular lens to be inserted.

The method and the system enable a reduction in postoperative refraction value errors, allowing determination of the power of an intraocular lens to be inserted based on the predicted intraocular lens.

The applicant of the present invention has previously proposed an optical coherence tomographic imaging apparatus (Non-Patent Literature 3). Unlike other commercially available products, the optical coherence tomographic imaging apparatus previously proposed by the applicant of the present invention can image even the posterior surface of the crystalline lens. This means that the shape of the crystalline lens can be accurately known.

That is, accurately knowing the shape of the crystalline lens capsule of a subject allows more accurate prediction of how a support section of the intraocular lens is fixed in the crystalline lens capsule and where an optical section is positioned. This reduces postoperative refraction errors to allow provision of a postoperative refraction value in line with the patients expectation.

Thus, an object of the present invention is, more specifically, to provide a method and a system that accurately determine the power of the intraocular lens to be inserted, based on a shape image of the crystalline lens obtained by the optical coherence tomographic imaging apparatus previously proposed by the applicant of the present invention. This enables a reduction in postoperative refraction value errors, allowing the optimum power of the intraocular lens to be determined.

A method to achieve the above purposes of the present invention for determining the power of intraocular lens to be inserted using a tomographic image of an anterior ocular segment generated by a tomographic imaging apparatus has a step of determining, by means of a computer, equator positions of a crystalline lens which correspond to the maximum diameter portion of the crystalline lens based on a morphology of the crystalline lens obtained from a tomographic image of the anterior ocular segment of a patients eye generated by the tomographic imaging apparatus, a step of estimating, by means of the computer, a distance from an anterior surface of a cornea, of an intraocular lens to be inserted, based on the determined equator positions, the anterior capsule position of the crystal lens and the posterior position of the crystal lens, and a step of determining, by means of the computer, the power of the intraocular lens, correspondingly to the estimated distance from the anterior surface of a cornea, of the intraocular lens to be inserted.

In an aspect of the method according to the present invention, the step of determining of the equator positions of the crystalline lens which correspond to the maximum diameter portion based on the morphology of the crystalline lens, which is generated by the tomographic imaging apparatus includes a step of approximating locus curves of an anterior capsule and of a posterior capsule of the crystalline lens based on shapes of the anterior capsule and the posterior capsule of the crystalline lens, and a step of determining, as the equator positions, intersecting points between the approximated locus curves of the anterior capsule of the crystalline lens and of the posterior capsule of the crystalline lens.

In an aspect of the method according to the present invention, the step of determining of, as the equator positions, the intersecting points between the approximated locus curves of the anterior capsule of the crystalline lens and of the posterior capsule of the crystalline lens has a step of setting a plurality of points along the shapes of the anterior capsule and the posterior capsule of the crystalline lens and generating polynomials which correspond to the shapes of the anterior capsule and the posterior capsule and which meet the set plurality of points, and a step of determining intersecting points between the generated polynomials as the equator positions of the crystalline lens which correspond to the maximum diameter portion.

In an aspect of the method according to the present invention, the step of determining, as the equator positions, the intersecting points between the approximated locus curves of the anterior capsule of the crystalline lens and of the posterior capsule of the crystalline lens has a step of expressing the locus curve of the anterior capsule of the crystalline lens and the locus curve of the posterior capsule of the crystalline lens as circular arcs extending along the shapes of the anterior capsule and the posterior capsule of the crystalline lens.

Moreover, in an aspect of the method according to the present invention, the intraocular lens position is estimated based on the determined equator positions, the anterior capsule position and the posterior position of the crystalline lens in accordance with a following formula:

$$\text{intraocular lens position} = 0.89 + 0.30 \times \text{anterior capsule position} + 0.25 \times \text{posterior capsule position} + 0.29 \times \text{equator positions},$$

where, on an ocular axial length passing through a center of a cornea, the anterior capsule position is a distance from an anterior surface of the cornea to a preoperative crystalline lens anterior capsule, and the posterior capsule position is a distance from the anterior surface of the cornea to a preoperative crystalline lens posterior capsule.

Moreover, another method that achieves the object of the present invention has a step of displaying, by means of a computer, a tomographic image of an anterior ocular segment of a patient's eye generated by the tomographic imaging apparatus, on a display apparatus, a step of determining, by means of the computer, as equator positions, positions input as intersecting points between extensions of locus curves of an anterior capsule and of a posterior capsule on the tomographic image of the patient's eye displayed on the display apparatus, the positions being input by an input unit in an instructive manner, a step of estimating, by means of the computer, a distance from an anterior surface of a cornea, of an intraocular lens to be inserted, based on the determined equator positions, the anterior capsule position of the crystal lens and the posterior position of the crystal lens, and a step of determining, by means of the computer, the power of the intraocular lens, correspondingly to the estimated distance from the anterior surface of a cornea, of the intraocular lens to be inserted.

DESCRIPTION OF PREFERRED EMBODIMENTS

An embodiment of the present invention will be described below with reference to the drawings.

Figure 2A:
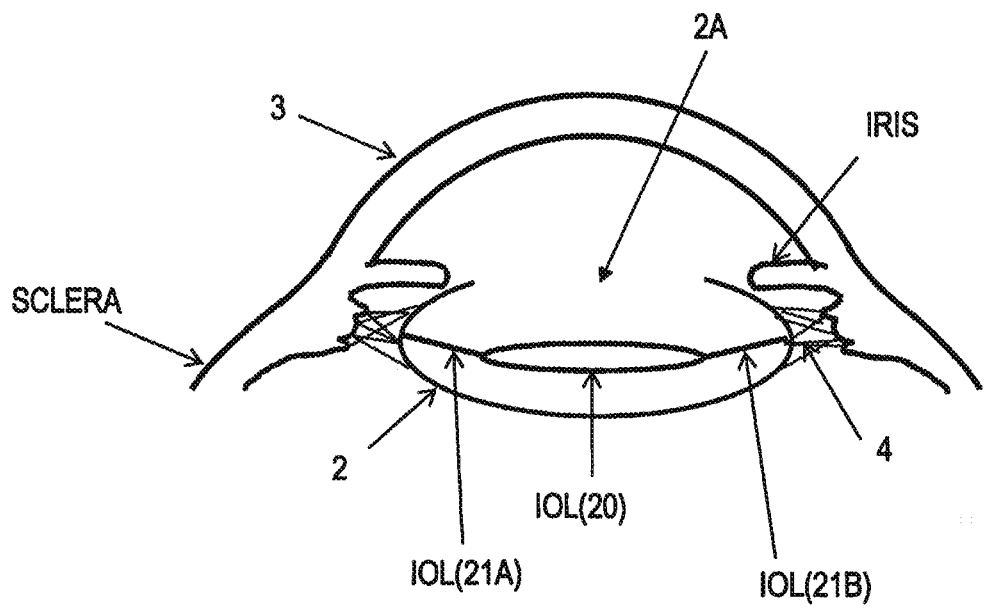
FIG. 2A and FIG. 2B are diagrams illustrating a configuration of an intraocular lens (hereinafter referred to as an IOL) embedded in a crystalline lens capsule instead of an opacified crystalline lens in a cataract operation.
Figure 2B:
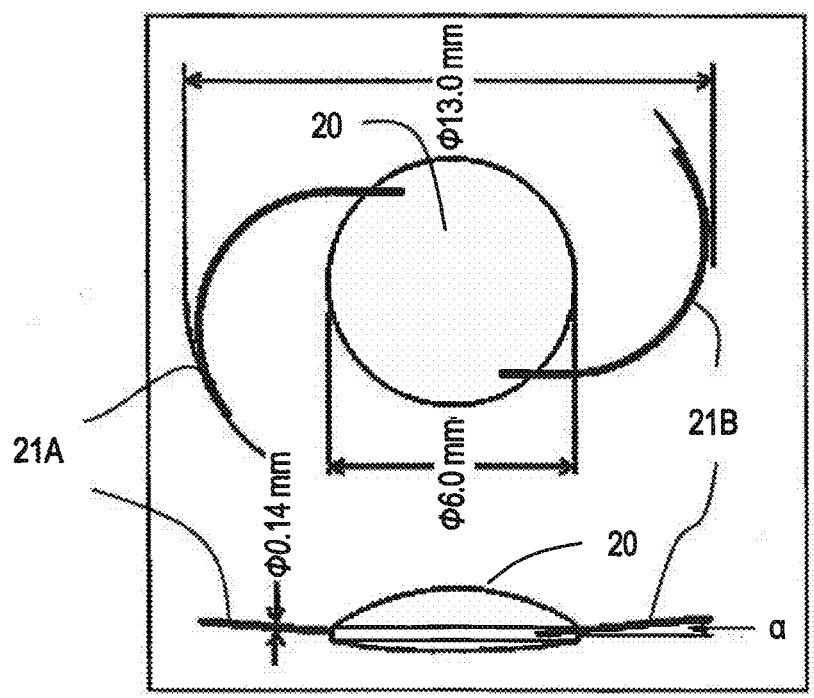

FIG. 2A and FIG. 2B are diagrams illustrating a configuration of an IOL embedded in the crystalline lens capsule instead of an opacified crystalline lens in a cataract operation. FIG. 2A is a schematic cross-sectional view of the IOL embedded in the crystalline lens capsule. FIG. 2B is a plan view and a side view of the IOL.

The IOL has an optical section 20 with a diameter of approximately 12.0 mm and support sections 21A and 21B extending from opposite sides of the optical section.

In FIG. 2A, the IOL is inserted into the crystalline lens capsule 2 through a hole 2A formed on a cornea 3 side of the crystalline lens capsule 2, that is, in the anterior capsule, while being folded because the IOL is formed of a flexible material. In the crystalline lens capsule 2, the IOL expands back to the original state and the support sections 21A and 21B are fixed like struts in the crystalline lens capsule 2. Each of the support sections 21A and 21B and the optical section 20 of the IOL define a given angle α (see FIG. 2B). Thus, knowing the positions of the support sections 21A and 21B allows the position of the optical section 20 to be estimated.

Then, it may be estimated that leading ends of the support sections 21A and 21B contact the crystalline lens capsule 2 at a maximum diameter position to position the IOL in the crystalline lens capsule. This is because the equator of the crystalline lens capsule 2 is 9.0 mm in diameter (reference: Ophthalmology, Toshio Maruo et al., 2002, BUNKODO CO., LTD), whereas the IOL is produced to have a diameter of approximately 12.0 mm, so that the support sections 21A and 21B are naturally positioned in the crystalline lens capsule 2 at the maximum diameter.

Moreover, the crystalline lens capsule 2 is fixed to an external tissue called a ciliary body via a tissue called the Zonule of Zinn 4. This fixation method remains unchanged after the operation. Thus, the preoperative site (equator) of the crystalline lens capsule 2 which has the maximum diameter is estimated not to be significantly different from the postoperative site.

Thus, according to the present invention, the position of the site (equator) of the crystalline lens capsule 2 which has the maximum diameter is estimated based on the preoperative shapes of the anterior capsule and the posterior capsule of the crystalline lens. The present invention is based on the concept that, given the support sections 21A and 21B of the IOL are fitted in the crystalline lens capsule 2 at the site (equator) where the crystalline lens capsule 2 has the maximum diameter, the position of the optical section 20 can be estimated based on the design of the IOL.

Moreover, a postoperative refraction value (the power of the crystalline lens) can be calculated based on the position of the IOL in the crystalline lens capsule 2.

Thus, according to the present invention, the postoperative position of the intraocular lens is predicted based on an optical coherence tomographic image of an anterior ocular segment imaged before operation. Therefore, based on the prediction, the postoperative refraction value (the power of the crystalline lens) can be accurately determined.

Figure 3:
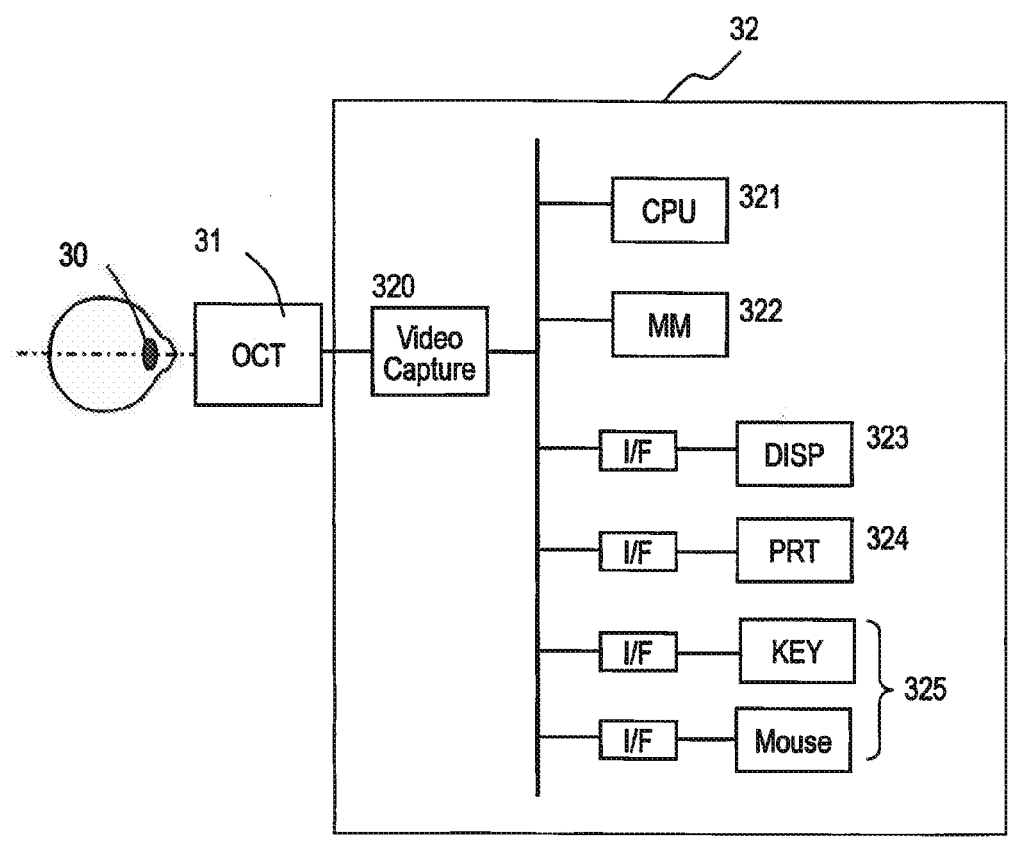
FIG. 3 is a block diagram of a configuration example of a system for estimating a postoperative position of an intraocular lens according to the present invention.

FIG. 3 is a block diagram of a configuration example of a system that implements the method for estimating a postoperative position of an intraocular lens using a tomographic image of the anterior ocular segment generated by the optical coherence tomographic imaging apparatus according to the present invention.

The system that estimates the postoperative position of the intraocular lens according to the present invention includes an OCT 31 that generates a tomographic image of the anterior ocular segment of a target eye 30 of a subject and an intraocular lens power calculation apparatus 32.

The OCT 31 is preferably an optical coherence tomographic imaging apparatus that uses the technique proposed in Non-Patent Literature 3 by the applicant as described above. That is, it is important to be able to obtain a tomographic image that allows determination of the morphology of the crystalline lens, particularly the shapes of the anterior capsule and the posterior capsule.

The tomographic image data on the target eye 30 obtained by the OCT 31 are delivered to the intraocular lens power calculation apparatus 32.

The intraocular lens power calculation apparatus 32 has a basic configuration that can be implemented by a personal computer. The method for estimating a postoperative position of an intraocular lens according to the present invention to determine the power of the intraocular lens to be inserted is implemented by a CPU 321 by executing a program stored in a memory 322.

The tomographic image data on the target eye 30 obtained by the OCT 31 are saved to the memory 322 through a video capture apparatus 320 of the intraocular lens power calculation apparatus 32. At the same time, the tomographic image is displayed on the display 323.

The intraocular lens power calculation apparatus 32 connects, via interfaces, to a printer 324 serving as an output apparatus and to a keyboard, a mouse, and the like serving as an input apparatus 325.

For the configuration in FIG. 3, an example using the OCT 31 has been illustrated as an aspect. However, the present invention is not limited to the example as long as tomographic images of the anterior capsule and posterior capsule of the crystalline lens can be captured. For example, Scheimpflug apparatus may also be used.

Figure 4:
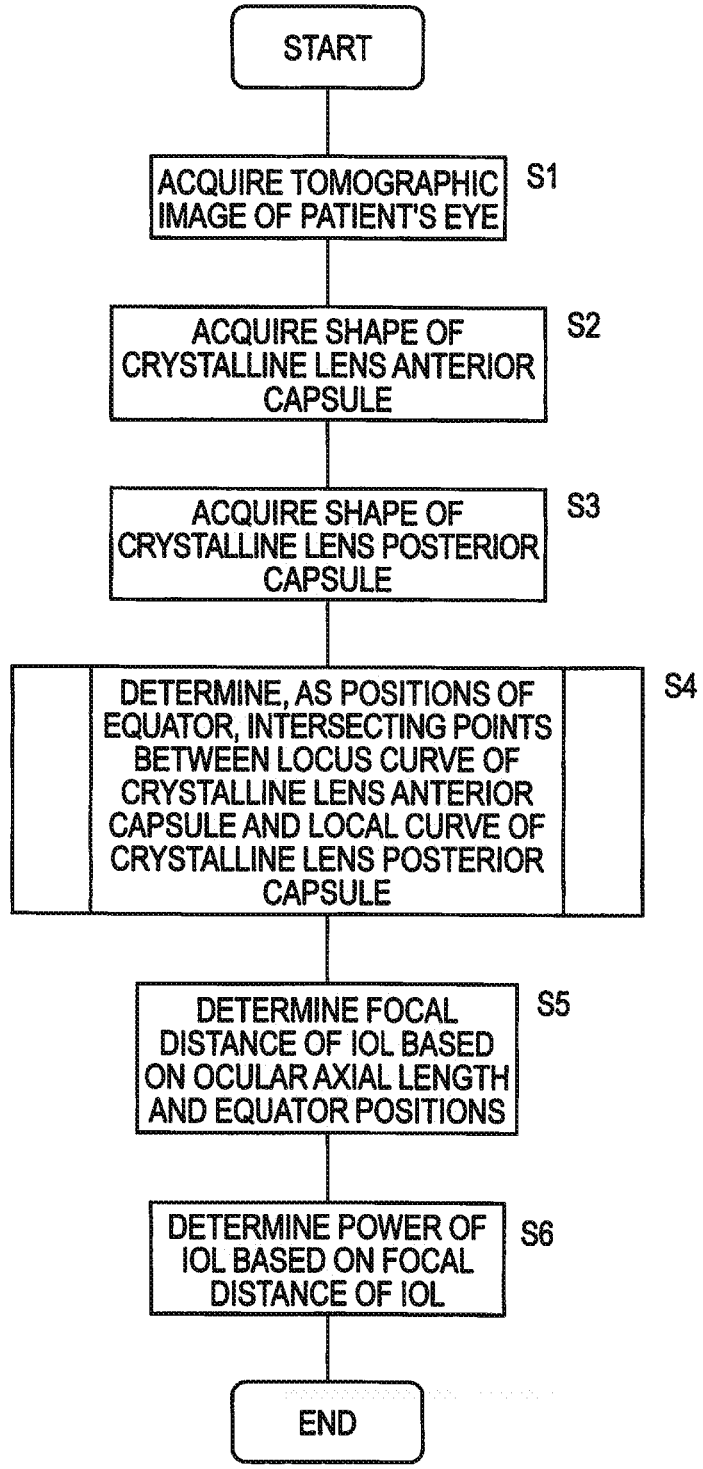
FIG. 4 is a flow diagram depicting a procedure for a method for reducing refraction errors resulting from a cataract operation which procedure is performed by the system for estimating the postoperative position of the intraocular lens.

FIG. 4 is a flowchart depicting a procedure executed under the control of the CPU 321 in the system that estimates the postoperative position of the intraocular lens.

Figure 5:
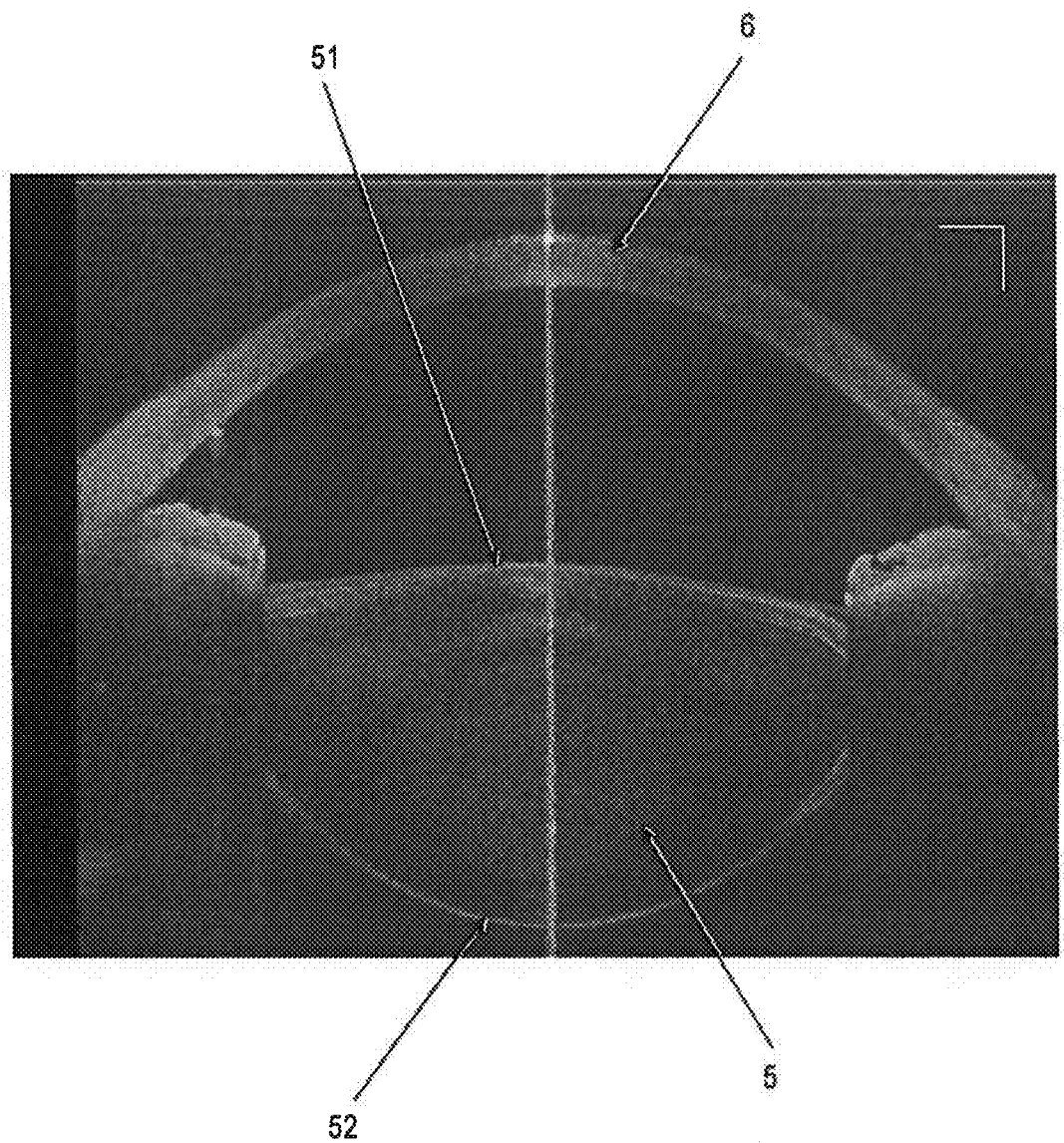
FIG. 5 is a diagram illustrating a tomographic image of the patients eye acquired by an optical coherence tomographic imaging apparatus (hereinafter referred to as OCT)

When the process starts, the OCT 31 acquires a tomographic image of the patients eye (step S1). FIG. 5 depicts an example of the tomographic image of the patients eye acquired by the OCT 31.

FIG. 5 depicts a cornea 6, a crystalline lens 5, a crystalline lens anterior capsule 51 on a cornea side of a crystalline lens capsule that envelopes the crystalline lens 5, and a crystalline lens posterior capsule 52 on the opposite side.

The procedure will further be described with reference back to FIG. 4. The morphology of the crystalline lens 5 is analyzed based on a tomographic image of the patients eye to determine the maximum diameter portion of the crystalline lens. Specifically, the shape of the crystalline lens anterior capsule 51 is determined (step S2), and further, the shape of the crystalline lens posterior capsule 52 is similarly determined (step S3).

Figure 6:
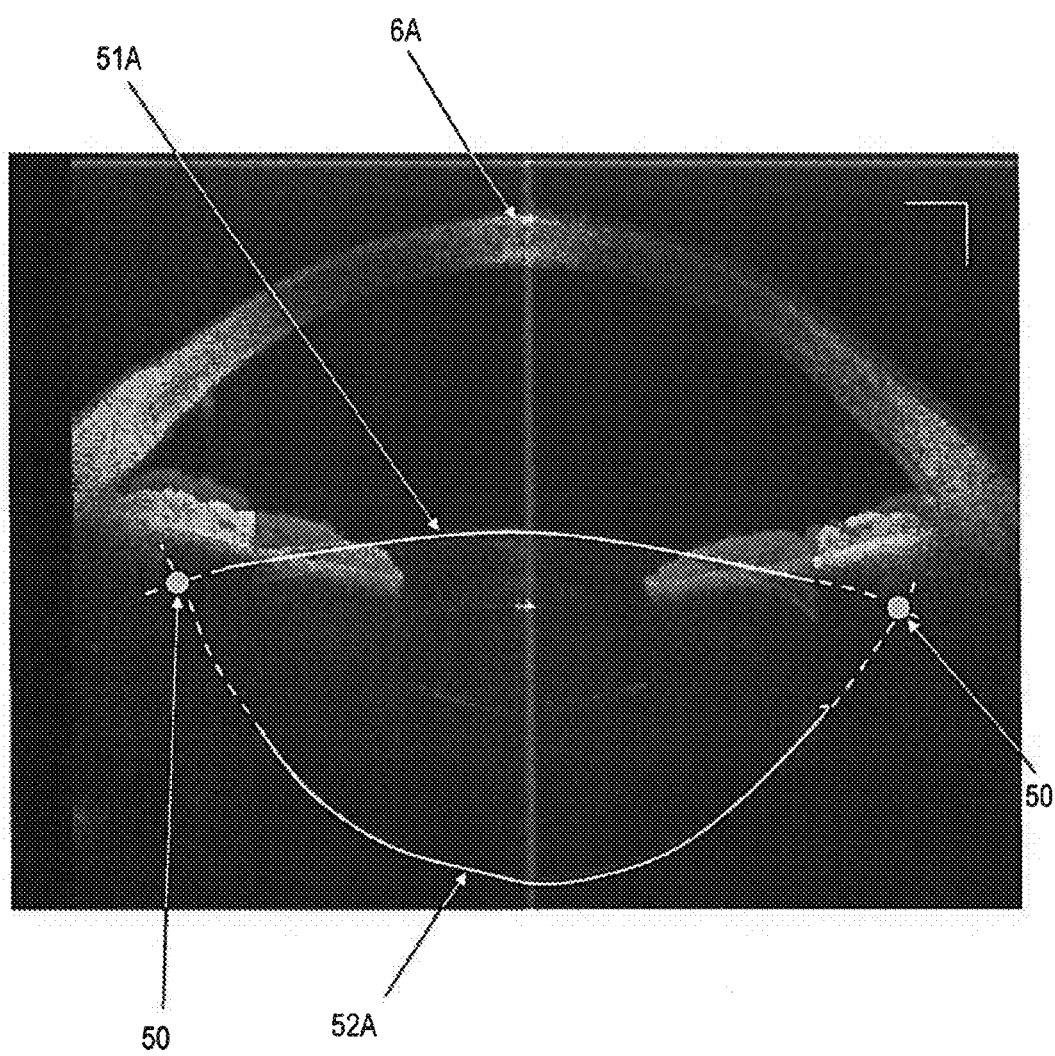
FIG. 6 is a schematic diagram depicting a state in which the shapes of a crystalline lens anterior capsule and a crystalline lens posterior capsule are determined by being approximated as locus curves.

FIG. 6 is a schematic diagram depicting a state in which the shape of the crystalline lens anterior capsule 51 is determined as a locus curve 51A by means of approximation and the shape of the crystalline lens posterior capsule 52 is determined as a locus curve 52A by means of approximation. FIG. 6 also depicts a locus curve 6A for the shape of the cornea 6.

In FIG. 6, areas (denoted by circles) located on the right and left of the locus curve 51A of the crystalline lens anterior capsule 51 and the locus curve 52A of the crystalline lens posterior capsule 52 are indiscriminable because light is blocked by the iris (see FIG. 2A) as illustrated in FIG. 5. However, the maximum diameter positions (equator) 50 of the crystalline lens capsule are present in these areas. It is then estimated that the support sections 21A and 21B of the intraocular lens (IOL) are positioned at the equator 50.

Moreover, according to the present invention, it is estimated that the equator 50 is present at intersecting points between extensions of the locus curve 51A of the crystalline lens anterior capsule 51 and the locus curve 52A of the crystalline lens posterior capsule 52, and the right and left positions of the equator 50 are determined (FIG. 4, step S4).

Figure 7:
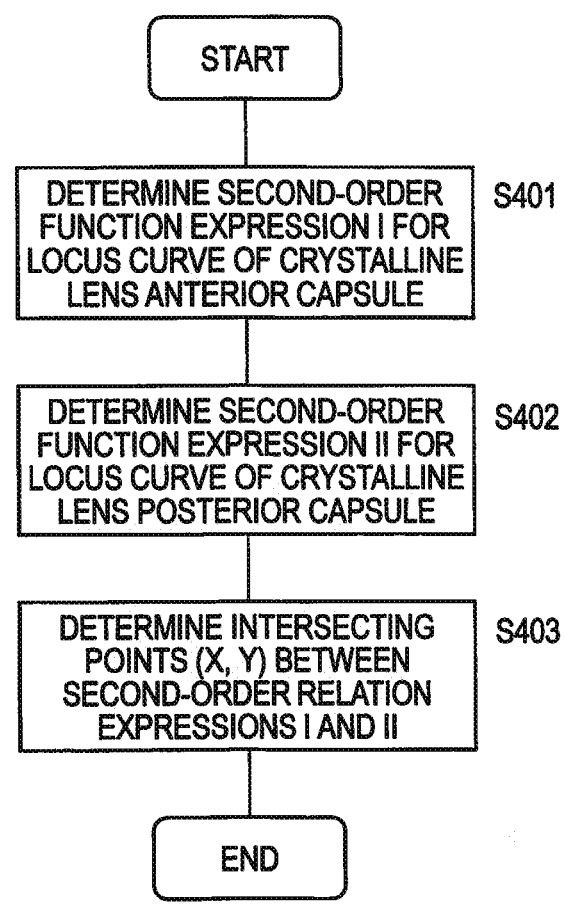
FIG. 7 is a detailed process flow of a first method for extending the locus curve of the crystalline lens anterior capsule and the locus curve of the crystalline lens posterior capsule to determine an intersecting point between the locus curves.

FIG. 7 is a detailed process flow of a first method for extending the locus curve 51A of the crystalline lens anterior capsule 51 and the locus curve 52A of the crystalline lens posterior capsule 52 to determine intersecting points between the locus curves 51A and 52A (step S4).

That is, a plurality of points is set on the locus curve 51A of the crystalline lens anterior capsule, and a locus meeting the conditions of the plurality of points is approximated using a polynomial, for example, a second-order relation expression I (step S401). Moreover, a plurality of points is similarly set on the locus curve 52A of the crystalline lens posterior capsule, and a locus meeting the conditions of the plurality of points is approximated using a polynomial, for example, a second-order relation expression II (step S402). Then, based on the two second-order relation expressions I and II, intersecting points (X, Y) on the loci where the relation expressions are equal are determined to determine equator points 50 (step S403).

Figure 8:
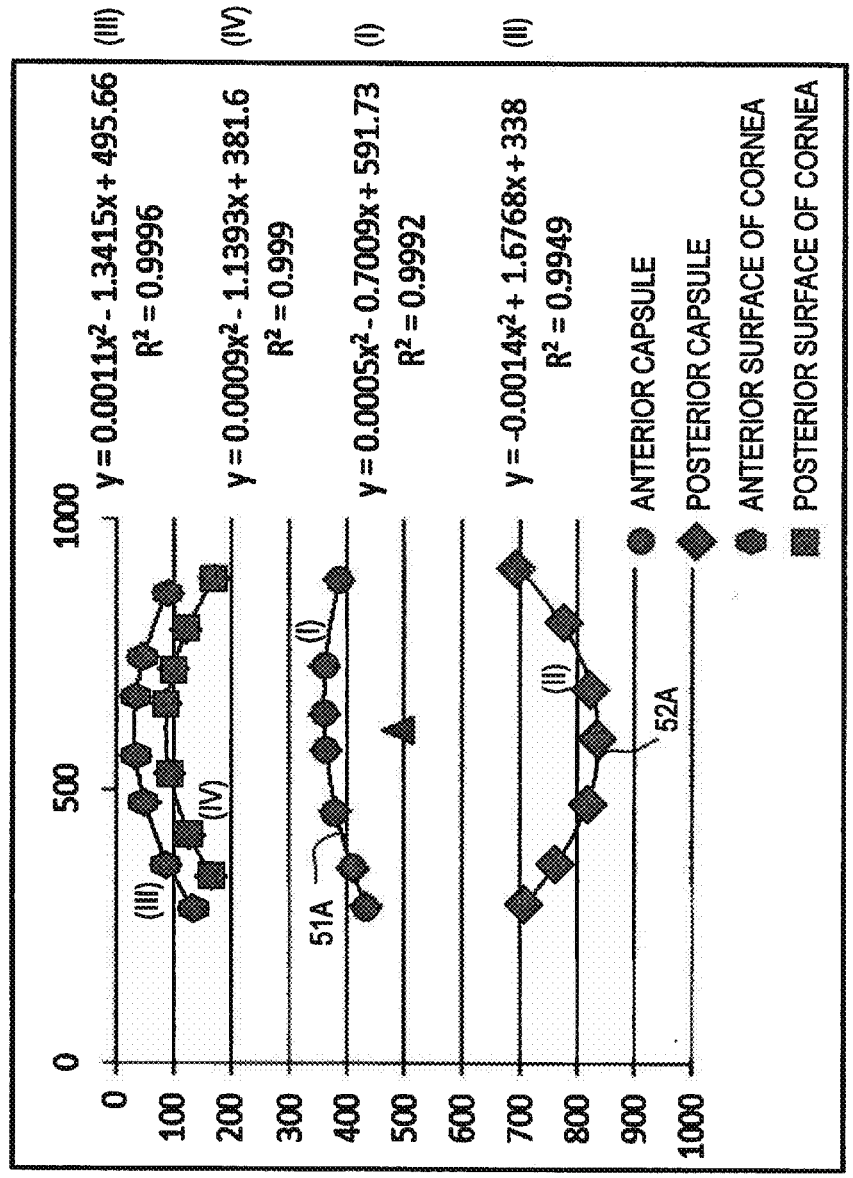
FIG. 8 is a diagram further illustrating a second-order relational expression determined in FIG. 7.

FIG. 8 is a diagram further illustrating the second-order relation expressions determined in FIG. 7. That is, second-order expressions may be determined which meet, for example, seven points set on each of the two locus curves, the locus curve 51A of the crystalline lens anterior capsule 51 and the locus curve 52A of the crystalline lens posterior capsule 52.

In an example depicted in FIG. 8, the second-order relation expression I representing the locus curve 51A of the crystalline lens anterior capsule 51 is:

$$y=0.0005x^2-0.7009x+591.73.$$

the second-order relation expression II representing the locus curve 52A of the crystalline lens posterior capsule 52 is:

$$y=-0.0014x^2+1.6768x+338.$$

Determining (X, Y) points where the two relation expressions are equal allows the equator points 50 to be determined as illustrated in FIG. 6.

FIG. 8 also depicts second-order relation expressions (III) and (IV) approximating an outer locus and an inner locus of the cornea 6 (FIG. 5).

Figure 9:
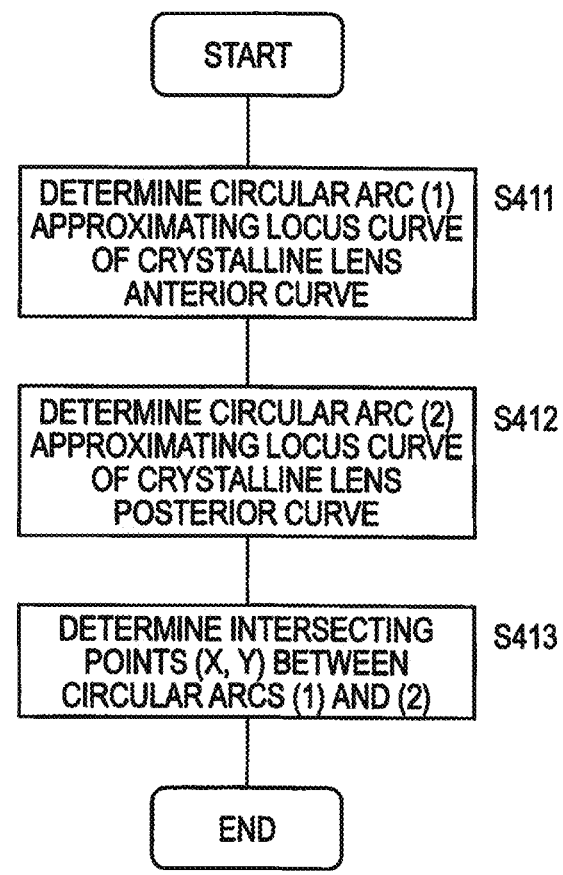
FIG. 9 is a detailed process flow of a second method for extending the locus curve of the crystalline lens anterior capsule and the locus curve of the crystalline lens posterior capsule to determine intersecting points between the locus curves.

FIG. 9 is a detailed process flow of a second method for extending the locus curve 51A of the crystalline lens anterior capsule 51 and the locus curve 52A of the crystalline lens posterior capsule 52 to determine intersecting points between the locus curves 51A and 52A (step S4).

That is, a first circular arc (1) approximating the locus curve 51A of the crystalline lens anterior capsule is determined (step S411). Moreover, a second circular arc (2) approximating the locus curve 52A of the crystalline lens posterior capsule is determined (step S412). Intersecting points between the two circular arcs (1) and (2) are determined as the equator 50 (step 413).

Figure 10:
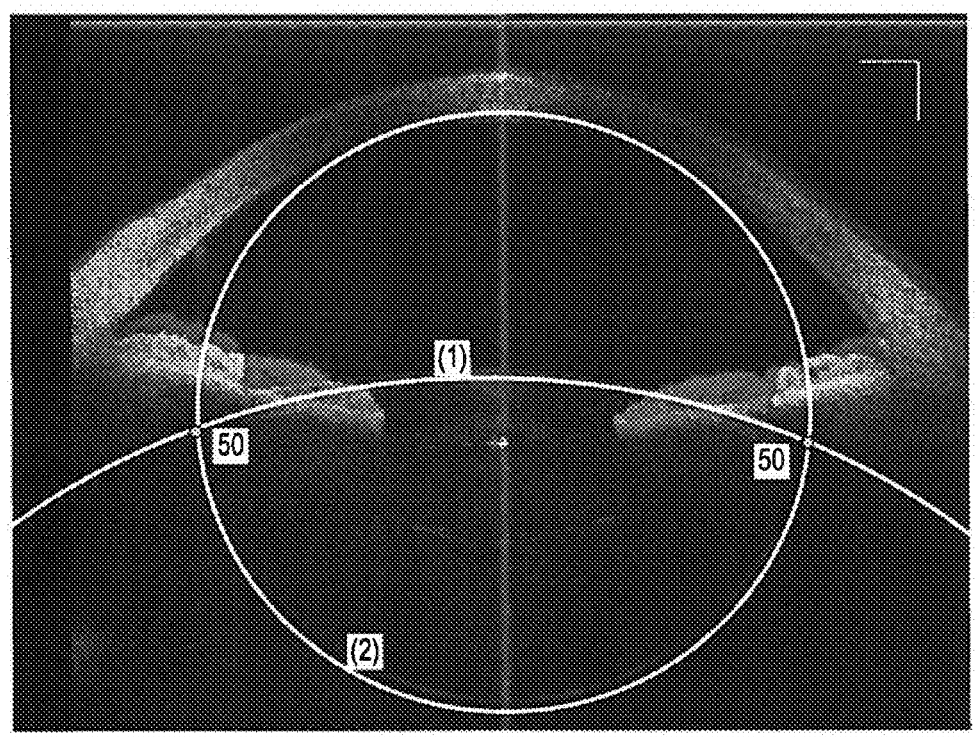
FIG. 10 is a diagram schematically depicting the second method.

FIG. 10 is a diagram schematically depicting the second method. The equator 50 is depicted as intersecting points between the approximated two circular arcs (1) and (2). Thus, the maximum diameter positions (50) of the crystalline lens capsule are determined.

The above-described embodiment discloses that the locus curve 51A of the crystalline lens anterior capsule 51 and the locus curve 52A of the crystalline lens posterior capsule 52 are approximated by polynomials, for example, second-order expressions or by circular arcs. However, the present invention is not limited to these approximation methods. It is also possible to perform any other curve approximation, for example, second- or higher-order polynomial curve approximation using ellipses, catenaries, or cubic curves, or approximation using trigonometric functions, exponential functions, or logarithmic functions.

The procedure will further be described with reference back to FIG. 4. When the equator 50 is determined as described above (step S4), positions in the crystalline lens capsule are estimated where the support sections 21A and 21B of the IOL are fixed. That is, it is estimated that the IOL is positioned by bringing the support sections 21A and 21B of the IOL into contact with the estimated equator positions 50.

Thus, the focal distance of the IOL is determined based on an ocular axial length L1 and the positions of the equator 50 (step S5). That is, the focal distance of the IOL is derived by subtracting the coordinate positions of the equator 50 from the ocular axial length L1.

Thus, the power of the IOL can be determined based on the determined focal distance of the IOL (step S6).

As described above, according to the present invention, the positions of the equator 50 are estimated based on the shape of the crystalline lens to determine the position of the IOL, allowing determination of the optimum power of the IOL to be used.

Moreover, the above-described embodiment also discloses that the first method and the second method involve, in determining the positions of the equator 50, calculating, by means of the computer, intersecting points between polynomials or circular arcs corresponding to locus curves of the anterior capsule and the posterior capsule. However, a tomographic image of the crystalline lens capsule imaged by the OCT 31 is displayed on a display 323, and intersecting points between extensions of the locus curves of the anterior capsule and of the posterior capsule are estimated at an operator's discretion. Then, the estimated intersecting points may be input and specified on the display 323 as the positions of the equator 50 by using, as input means, a touch panel or cursor movement via a mouse.

Figure 11:
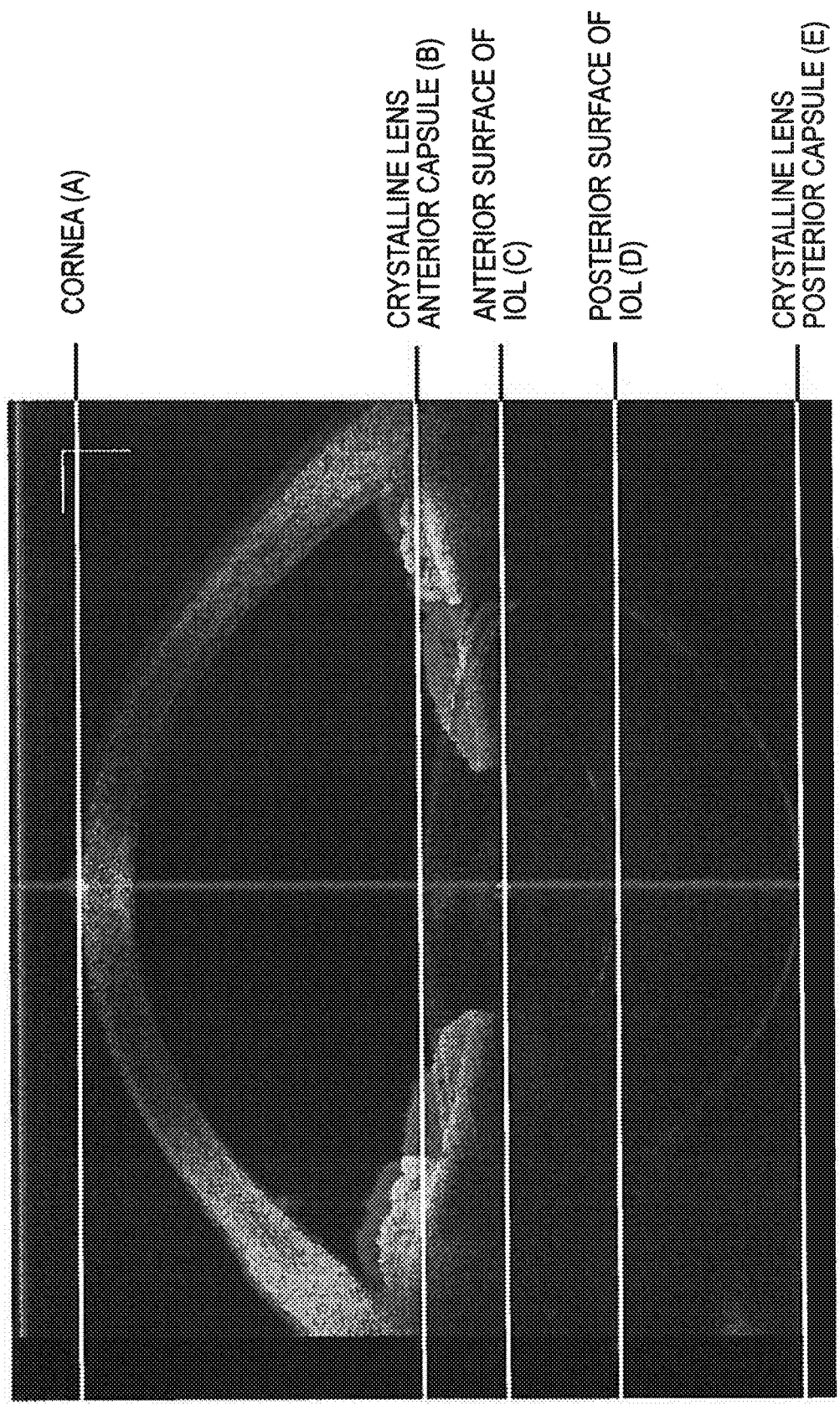
FIG. 11 is an image displayed by superimposing an postoperative tomographic image on a preoperative tomographic image (see FIG. 5)

FIG. 11 is an image displayed by superimposing a postoperative tomographic image on a preoperative tomographic image (see FIG. 5). The postoperative tomographic image depicts an inserted intraocular lens (IOL). The positions of the cornea surface (A), the crystalline lens anterior capsule (B), the IOL anterior surface (C), the IOL posterior surface (D), and the crystalline lens posterior capsule (E) have been written in FIG. 11.

Figure 12:
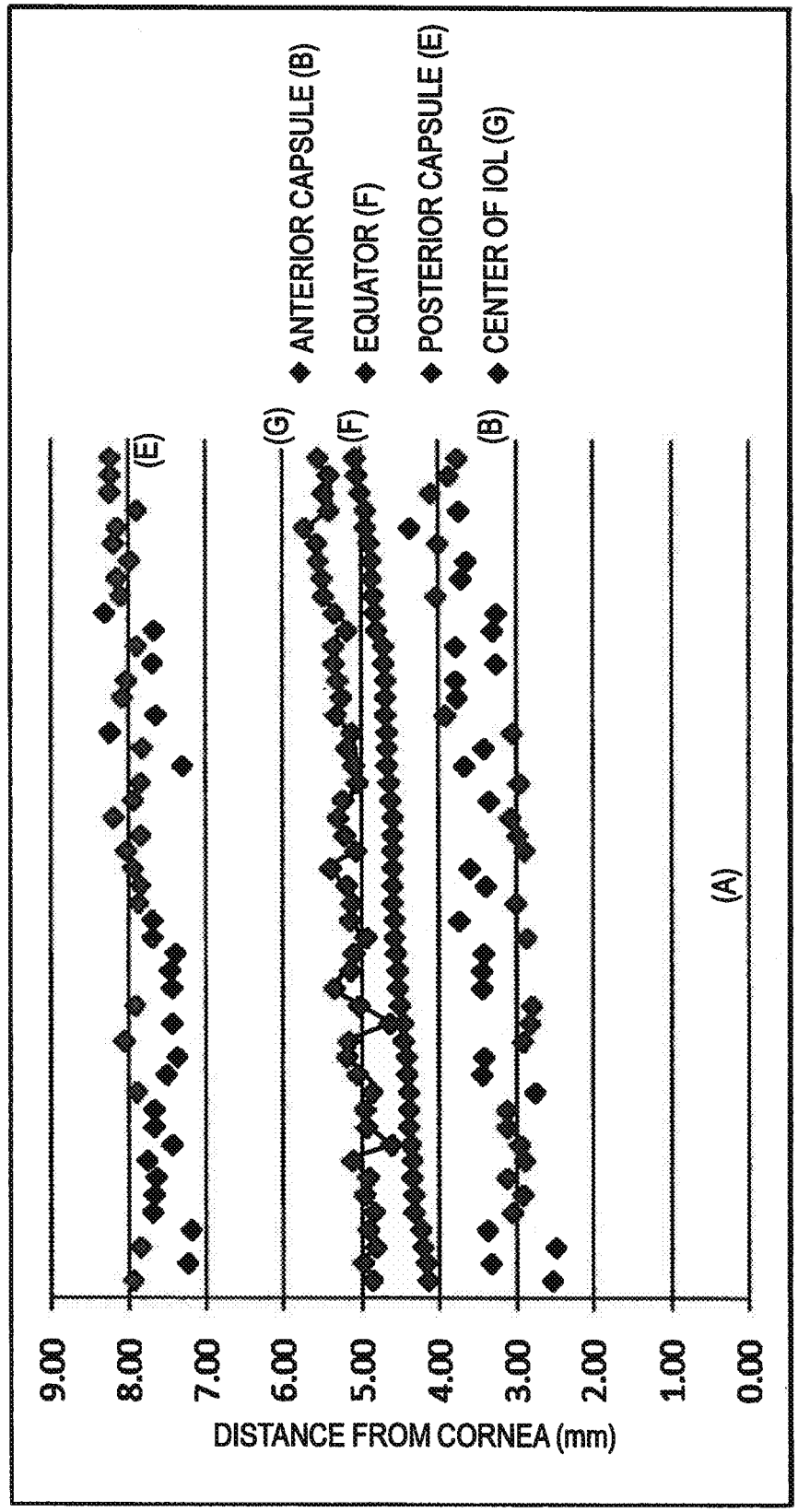
FIG. 12 is a graph in which data on positional relations among the (A) cornea surface, the (B) crystalline lens anterior capsule, the (E) crystalline lens posterior capsule, the (F) equator, and the (G) IOL center are plotted for a plurality of patients.

FIG. 12 depicts a graph in which data, of a plurality of patients, on the relations among the above-described positions are plotted. In FIG. 12, the axis of abscissas indicates patient samples, and the axis of ordinate indicates the distance from the cornea surface (A). That is, FIG. 12 depicts the crystalline lens anterior capsule (B), the crystalline lens posterior capsule (E), and a value for the center (G) between the IOL anterior surface (C) and the IOL posterior surface (D) all of which have been corrected based on the refractive index, with the position of the cornea surface (A) set to 0.00. Moreover, the position of the equator (F) estimated by the method according to the present invention is plotted.

In FIG. 12, points representing the plotted positions of the IOL center (G) are connected together with a line in order to clearly distinguish the position of the equator (F) from the position of the IOL center (G).

The relations in FIG. 12 clearly indicates that all the positions of the equator (F) lie approximately at a constant distance from the IOL center value (G) on the anterior side (anterior capsule side). Thus, this statistical graph clearly indicates that the present invention allows the equator to be estimated to enable the lens position to be substantially accurately determined.

Figure 13:
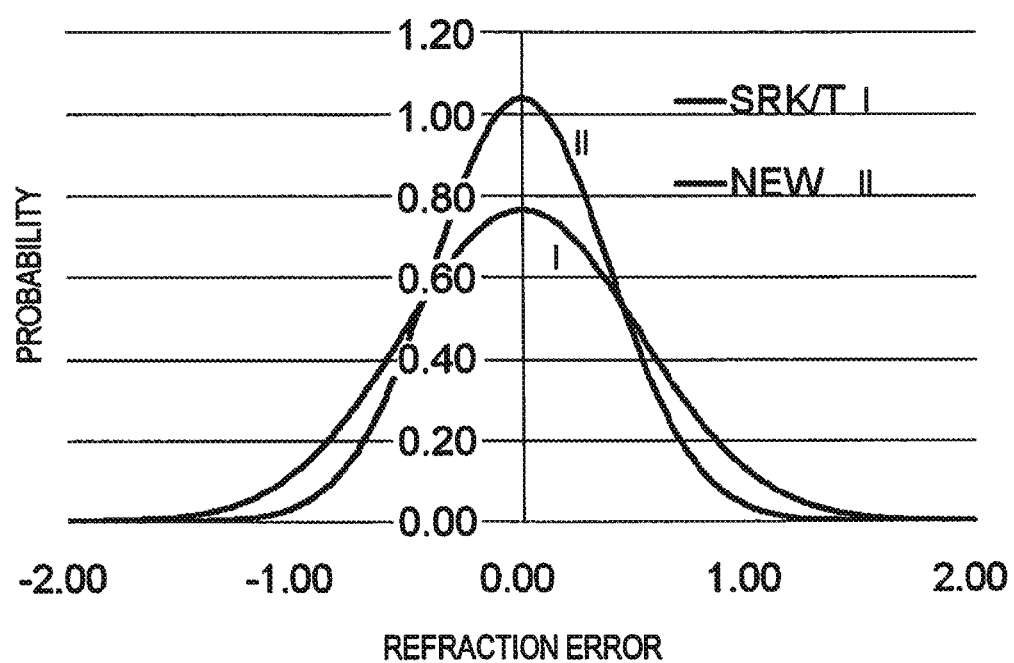
FIG. 13 is a diagram depicting the probability distribution of refraction errors in which the SRK/T scheme and the present invention are compared with each other.

Moreover, FIG. 13 depicts the probability distribution of refraction errors according to the present invention compared to the probability distribution of refraction errors according to the conventional SRK/T scheme, used in approximately 60% of all the cases. In FIG. 13, the probability distributions may be considered to be normal distributions. The probability of having an error larger than 0.5D is 33.9% when based on the IOL position determined in accordance with the conventional SRK/T scheme, whereas the refraction error is 19.4% in the case of an IOL power determined based on the position of the equator determined by the method according to the present invention. Moreover, the probability of having an error larger than 1D is 5.59% when based on the conventional SRK/T scheme but is 0.94% when based on the method according to the present invention.

This also clearly indicates that application of the method according to the present invention enables more accurate estimation of the IOL position to be used.

Figure 1:
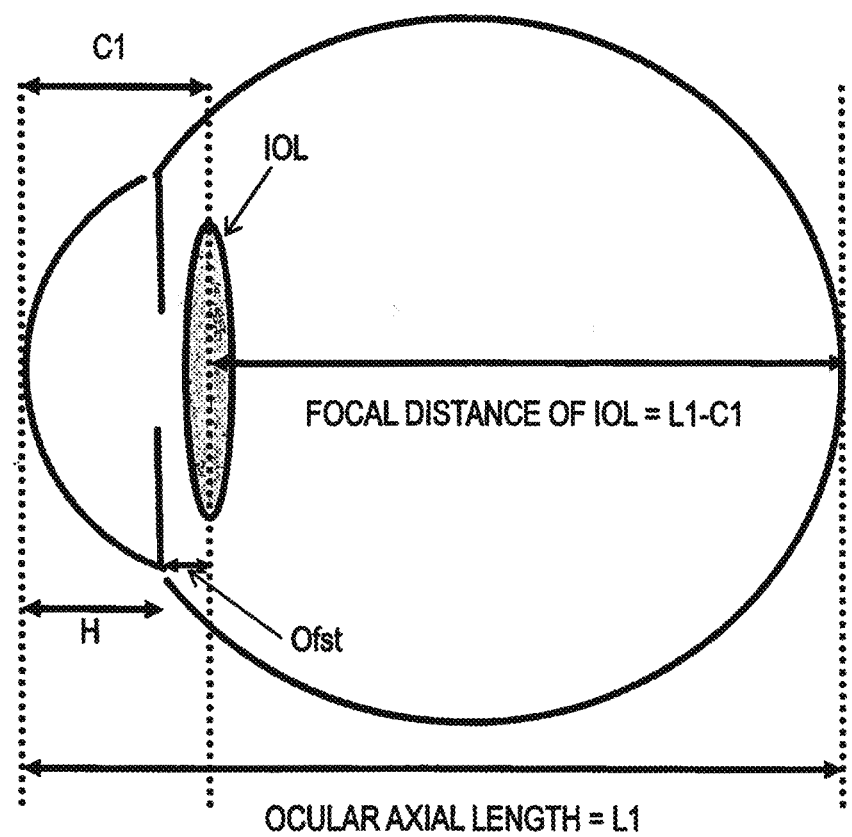
FIG. 1 is a diagram schematically depicting an insertion position of an intraocular lens for description of an SRK/T scheme.

Moreover, the inventors evaluated the effects of the present invention using the framework of the SRK/T. That is, a prediction expression was generated which allows a postoperative predicted anterior chamber depth C1 (see FIG. 1) to be calculated using, as parameters, the preoperative position of the crystalline lens anterior capsule and the preoperative position of the crystalline lens posterior capsule obtained from a plurality of patients, and the position of the equator determined by the above-described method. The prediction expression varies depending on a case of the cataract and the type of the intraocular lens.

$$C1 \text{ (mm)} = 0.89 + 0.30 \times \text{the anterior capsule position} + 0.25 \times \text{the posterior capsule position} + 0.29 \times \text{the equator position}$$

In this regard, the anterior capsule position and the posterior capsule position refer to the positions of the anterior capsule and the posterior capsule which cross the ocular axial length passing through the center of the cornea.

Then, the prediction expression was applied to a plurality of patients different from the above-described plurality of patients, and the postoperative refraction error was evaluated. Even in this situation with autoregression inhibited, the new prediction expression significantly reduced error variances.

As described above, the present invention involves estimating the equator positions of the crystalline lens, which correspond to the maximum diameter portion, based on the morphology of the crystalline lens obtained from a tomographic image taken by the OCT using optical coherence, enabling the postoperative position of the IOL to be predicted based on the estimated equator positions. Based on the predicted postoperative position of the IOL, the accurate refraction value of the IOL can be determined. This allows the postoperative satisfaction of the cataract patient to be further improved.

The insertion of the intraocular lens has been described above exclusively for the case of the cataract. However, the present invention is not limited to this application but is applicable even when an intraocular lens is inserted for treatment of glaucoma or the like.

The invention claimed is:

1. A method for determining the power of intraocular lens to be inserted using a tomographic image of an anterior ocular segment generated by a tomographic imaging apparatus, the method comprising:

determining, by means of a computer, equator positions of a crystalline lens which correspond to the maximum diameter portion of the crystalline lens based on a morphology of the crystalline lens obtained from a tomographic image of the anterior ocular segment of a patient's eye generated by the tomographic imaging apparatus;

estimating, by means of the computer, a distance from an anterior surface of a cornea, of an intraocular lens to be inserted, based on the determined equator positions, the anterior capsule position of the crystal lens and the posterior position of the crystal lens; and determining, by means of the computer, the power of the intraocular lens, correspondingly to the estimated distance from the anterior surface of a cornea, of the intraocular lens to be inserted, wherein the determining of the equator positions of the crystalline lens which correspond to the maximum diameter portion based on the morphology of the crystalline lens, which is generated by the tomographic imaging apparatus includes:

approximating locus curves of an anterior capsule and of a posterior capsule of the crystalline lens based on shapes of the anterior capsule and the posterior capsule of the crystalline lens, and determining, as the equator positions, intersecting points between the approximated locus curves of the anterior capsule of the crystalline lens and of the posterior capsule of the crystalline lens.

2. The method for determining the power of intraocular lens to be inserted according to claim 1, wherein the determining of, as the equator positions, the intersecting points between the approximated locus curves of the anterior capsule of the crystalline lens and of the posterior capsule of the crystalline lens includes:

setting a plurality of points along the shapes of the anterior capsule and the posterior capsule of the crystalline lens and generating polynomials which correspond to the shapes of the anterior capsule and the posterior capsule and which meet the set plurality of points; and determining intersecting points between the generated polynomials as the equator positions of the crystalline lens which correspond to the maximum diameter portion.

3. The method for determining the power of intraocular lens to be inserted according to claim 1, wherein the determining of, as the equator positions, the intersecting points between the approximated locus curves of the anterior capsule of the crystalline lens and of the posterior capsule of the crystalline lens includes:

expressing the locus curve of the anterior capsule of the crystalline lens and the locus curve of the posterior capsule of the crystalline lens as circular arcs extending along the shapes of the anterior capsule and the posterior capsule of the crystalline lens.

4. The method for determining the power of intraocular lens to be inserted according to claim 1, further comprising estimating the intraocular lens position based on the determined equator positions, the anterior capsule position and the posterior position of the crystalline lens in accordance with a following formula:

intraocular lens position=0.89+0.30×anterior capsule position+0.25×posterior capsule position+0.29× equator positions, where, on an ocular axial length passing through a center of a cornea, the anterior capsule position is a distance from an anterior surface of the cornea to a preoperative crystalline lens anterior capsule, and the posterior capsule position is a distance from the anterior surface of the cornea to a preoperative crystalline lens posterior capsule.

5. A method for determining the power of intraocular lens to be inserted using a tomographic image of an anterior ocular segment generated by a tomographic imaging apparatus, the method comprising:

displaying, by means of a computer, a tomographic image of an anterior ocular segment of a patient's eye generated by the tomographic imaging apparatus, on a display apparatus; and approximating, by means of the computer, on the tomographic image of the patient's eye displayed on the display apparatus, locus curves of an anterior capsule and of a posterior capsule of a crystalline lens based on shapes of the anterior capsule and the posterior capsule of the crystalline lens;

determining, by means of the computer, as equator positions, positions input as intersecting points between extensions of the approximated locus curves of an anterior capsule and of a posterior capsule, the positions being input by an input unit in an instructive manner;

estimating, by means of the computer, a distance from an anterior surface of a cornea, of an intraocular lens to be inserted, based on the determined equator positions, the anterior capsule position of the crystal lens and the posterior position of the crystal lens; and determining, by means of the computer, the power of the intraocular lens, correspondingly to the estimated distance from the anterior surface of a cornea, of the intraocular lens to be inserted.

6. A system for determining the power of intraocular lens to be inserted using a tomographic image of an anterior ocular segment generated by a tomographic imaging apparatus, the system comprising:

a tomographic imaging apparatus configured to generate a tomographic image of a patient's eye;

a unit configured to determine equator positions of a crystalline lens which correspond to a maximum diameter portion based on a morphology of the crystalline lens obtained from the tomographic image of the patient's eye generated by the tomographic imaging apparatus; and a unit configured to estimate a distance from an anterior surface of a cornea, of an intraocular lens to be inserted, based on the determined equator positions, the anterior capsule position of the crystal lens and the posterior position of the crystal lens; and a unit configured to determine the power of the intraocular lens, correspondingly to the estimated distance from the anterior surface of a cornea, of the intraocular lens to be inserted, wherein the unit configured to determine the equator positions of the crystalline lens which correspond to the maximum diameter portion based on the morphology of the crystalline lens includes:

a unit configured to approximate locus curves of an anterior capsule and of a posterior capsule of the crystalline lens based on shapes of the anterior capsule and the posterior capsule, and a unit configured to determine, as the equator positions, intersecting points between the approximated locus curves of the anterior capsule of the crystalline lens and of the posterior capsule of the crystalline lens.

7. The system for determining the power of intraocular lens to be inserted according to claim 6, wherein the unit configured to determine the equator positions of the crystalline lens which correspond to the maximum diameter portion based on the morphology of the crystalline lens includes:

a unit configured to set a plurality of points along the shapes of the anterior capsule and the posterior capsule of the crystalline lens and generate polynomials which correspond to the shapes of the anterior capsule and the posterior capsule and which meet the set plurality of points; and a unit configured to determine intersecting points between the generated polynomials as the equator positions of the crystalline lens which correspond to the maximum diameter portion.

8. The system for determining the power of intraocular lens to be inserted according to claim 6, wherein the unit configured to determine the equator positions of the crystalline lens which correspond to the maximum diameter portion based on the morphology of the crystalline lens, when determining, as the equator positions, the intersecting points between the approximated locus curves of the anterior capsule of the crystalline lens and of the posterior capsule of the crystalline lens, expresses the locus curve of the anterior capsule of the crystalline lens and the locus curve of the posterior capsule of the crystalline lens as circular arcs extending along the shapes of the anterior capsule and the posterior capsule of the crystalline lens.

9. The system for determining the power of intraocular lens to be inserted according to claim 6, wherein the unit configured to determine the equator positions of the crystalline lens which correspond to the maximum diameter portion based on the morphology of the crystalline lens estimates the intraocular lens position based on the determined equator positions, and positions of the anterior capsule and the posterior capsule of the crystalline lens in accordance with a following formula:

intraocular lens position=0.89+0.30×anterior capsule position+0.25×posterior capsule position+0.29× equator positions, where, on an ocular axial length passing through a center of a cornea, the anterior capsule position is a distance from an anterior surface of the cornea to a preoperative crystalline lens anterior capsule, and the posterior capsule position is a distance from the anterior surface of the cornea to a preoperative crystalline lens posterior capsule.

10. A system for determining the power of a postoperative intraocular lens comprising:

a tomographic imaging apparatus for configured to generate a tomographic image of an anterior ocular lens of a patient's eye;

a display apparatus configured to display the tomographic image of the anterior ocular lens of the patient's eye generated by the tomographic imaging apparatus;

a unit configured to approximate, by means of the computer, on the tomographic image of the patient's eye displayed on the display apparatus, locus curves of an anterior capsule and of a posterior capsule of a crystalline lens based on shapes of the anterior capsule and the posterior capsule of the crystalline lens;

an input unit configured to enable intersecting points between extensions of the approximated locus curves of an anterior capsule and of a posterior capsule to be input in an instructive manner on the tomographic image of the patient's eye displayed on the display apparatus;

a determining unit configured to determine, as equator positions, the intersecting points between the extensions of the locus curves of the anterior capsule and of the posterior capsule input by the input unit; and a unit configured to estimate, by means of the computer, a distance from an anterior surface of a cornea, of an intraocular lens to be inserted, based on the determined equator positions, the anterior capsule position of the crystal lens and the posterior position of the crystal lens;

a determination unit configured to determine the power of the intraocular lens, correspondingly to the estimated distance from the anterior surface of a cornea, of the intraocular lens to be inserted.

* * * * *